United States Patent
Lee

(10) Patent No.: US 8,157,762 B2
(45) Date of Patent: Apr. 17, 2012

(54) PORTABLE MEDICAL LIQUID INFUSION DEVICE

(75) Inventor: Doo Yong Lee, Daejeon (KR)

(73) Assignees: Hanvit MD Co., Ltd, Daejeon (KR); Doo Yong Lee

( * ) Notice: Subject to any disclaimer, the term of this patent is extended or adjusted under 35 U.S.C. 154(b) by 0 days.

(21) Appl. No.: 12/980,049

(22) Filed: Dec. 28, 2010

(65) Prior Publication Data

US 2011/0160651 A1    Jun. 30, 2011

(30) Foreign Application Priority Data

Dec. 31, 2009   (KR) .................. 10-2009-0135308

(51) Int. Cl.
    *A61M 5/14*   (2006.01)
(52) U.S. Cl. ........................................ 604/65
(58) Field of Classification Search .......... 604/65, 604/66; 600/345, 454, 458; 73/1.16
    See application file for complete search history.

(56) References Cited

U.S. PATENT DOCUMENTS

| | | | |
|---|---|---|---|
| 4,321,461 A * | 3/1982 | Walter et al. | 377/21 |
| 4,832,689 A * | 5/1989 | Mauerer et al. | 604/67 |
| 4,938,072 A * | 7/1990 | Brown et al. | 73/861 |
| 5,116,312 A * | 5/1992 | Blankenship et al. | 604/66 |
| 5,395,320 A * | 3/1995 | Padda et al. | 604/65 |
| 7,055,366 B2 * | 6/2006 | Lewis | 73/1.16 |
| 7,311,691 B2 * | 12/2007 | Cartledge et al. | 604/65 |
| 7,516,641 B2 * | 4/2009 | Lewis | 73/1.16 |

* cited by examiner

*Primary Examiner* — Nicholas Lucchesi
*Assistant Examiner* — Aarti B Berdichevsky

(57) ABSTRACT

A portable medical liquid infusion device receives an input of a medical liquid infusion rate (cc/hour), the quantity of medical liquid to be infused or the length of time for infusion, and outputs a recognition signal corresponding to the input, thereby allowing a drip interval to be easily adjusted, and which quantitatively calculates and outputs a medical liquid infusion rate on the basis of a count input which is received in accordance with a drip interval when measuring the medical liquid infusion rate. The medical liquid infusion device judges a count input having an irregular interval as an erroneous input, and renders another count input to be conducted again through automatic resetting, whereby the medical liquid infusion device can output a correct measurement result only, and also can output the length of time for infusing the remaining medical liquid when measuring the medical liquid infusion rate.

3 Claims, 3 Drawing Sheets

[Fig.1]
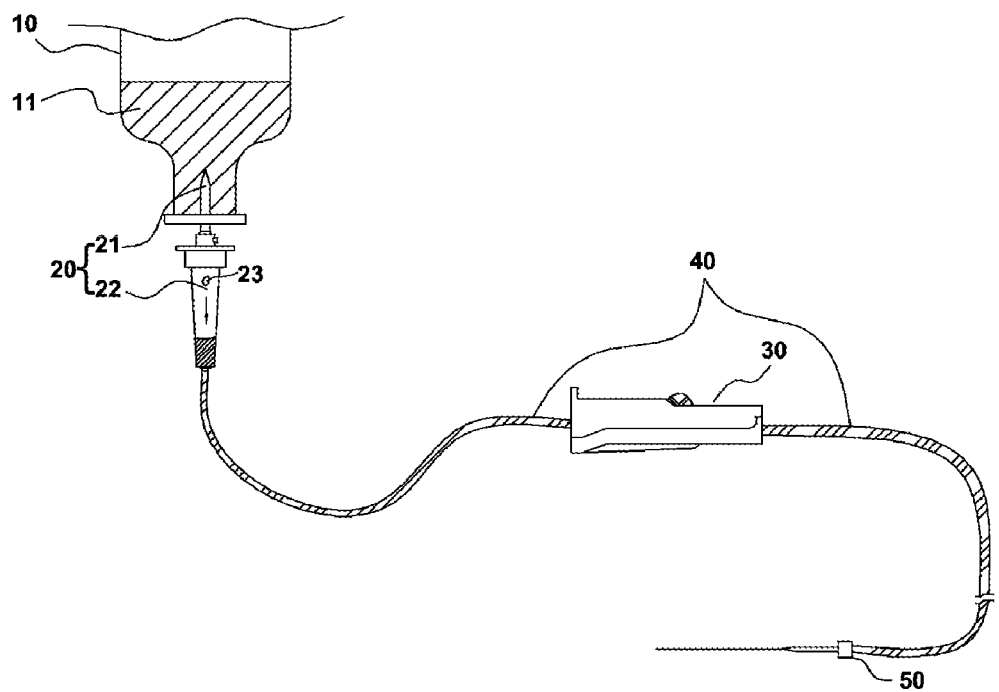

[Fig. 2]
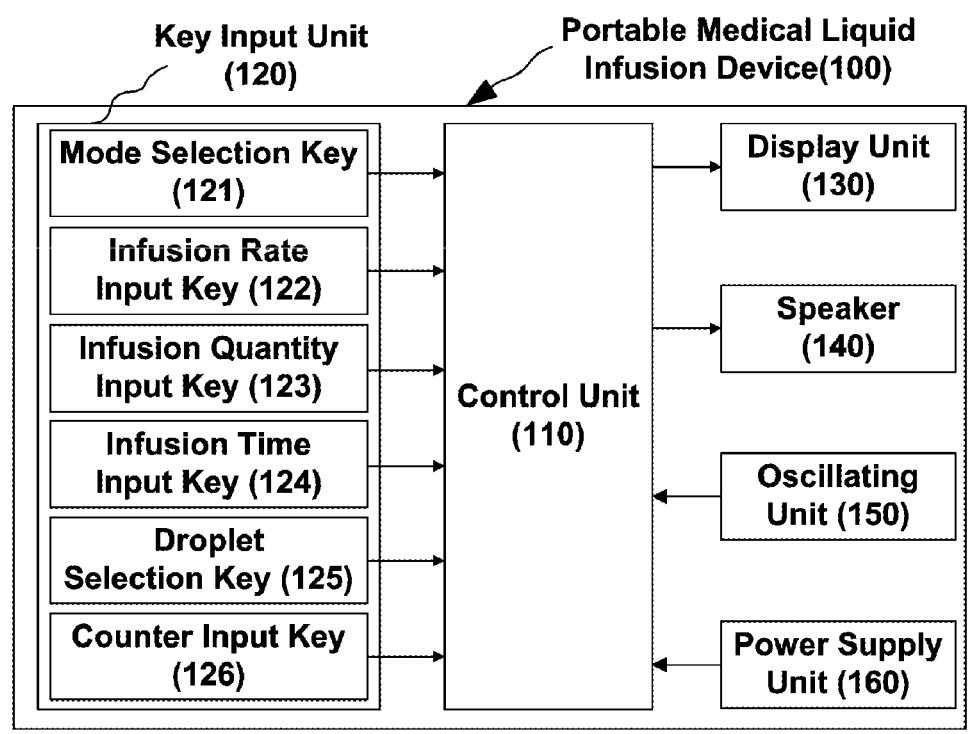

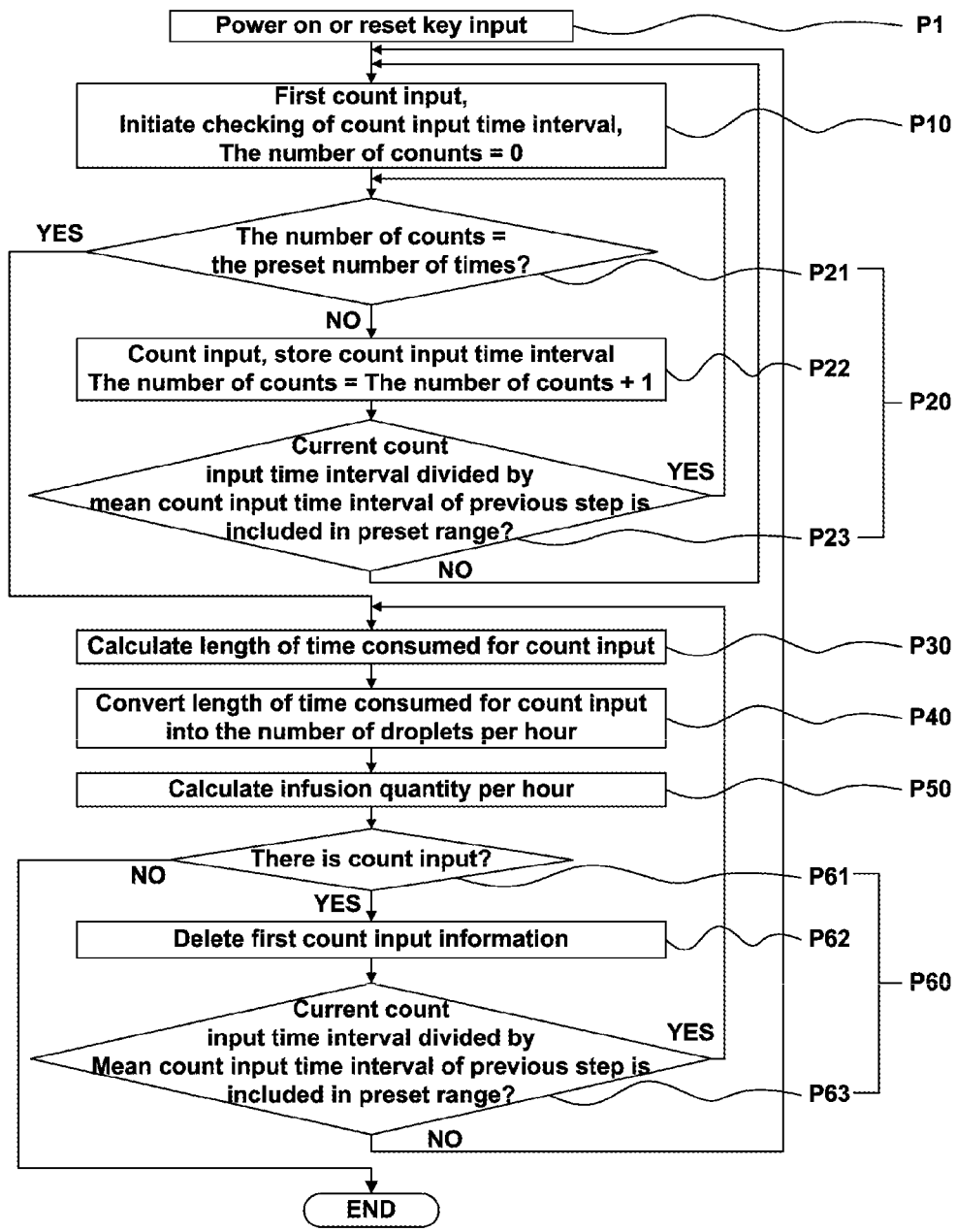
[Fig. 3]

PORTABLE MEDICAL LIQUID INFUSION DEVICE

BACKGROUND OF THE INVENTION

1. Field of the Invention

The present invention relates to a portable medical liquid infusion device which is capable of quantitatively measuring medical liquid infusion rate, and of informing a drip interval by a recognizable signal when the medical liquid infusion rate is adjusted. More particularly, the present invention relates to a portable medical liquid infusion device which receives an input of a medical liquid infusion rate (cc/hour), the quantity of medical liquid to be infused, or the length of time for infusion, and outputs a recognition signal corresponding to the input, thereby allowing a drip interval to be easily adjusted, and which quantitatively calculates and outputs a medical liquid infusion rate on the basis of a count input which is received in accordance with a drip interval when measuring the medical liquid infusion rate, wherein the medical liquid infusion device judges a count input having an irregular interval as an erroneous input, and renders another count input to be made again through automatic resetting, whereby the medical liquid infusion device can output a correct measurement result only, and also can output the length of time for infusing the remaining medical liquid when measuring the medical liquid infusion rate.

2. Description of the Prior Art

Referring to FIG. 1, a conventional intravenous (IV) injection system for directly administrating medical liquid to a vein includes: a medical liquid bottle 10 in which medical liquid 11 is contained; a dripper 20 consisting of an insertion needle 21 inserted through a sealing plug of the medical liquid bottle 10, so that the medical liquid 11 flows through the insertion needle 21, and a drip chamber 22 within which the medical liquid 11 drops in the form of droplets 23; an injection needle 50 inserted into a vein; an infusion tube 40 interconnecting the dripper 20 and the injection needle 50 so that the medical liquid flows through the infusion tube 40; and a medical liquid regulator 30 fitted on a middle part of the infusion tube so as to regulate the flow rate of the medical liquid.

Intravenous infusion using the above-mentioned IV system is conducted by fixedly positioning the medical liquid bottle 10 above the injection needle 50, so that the medical liquid 11 can be naturally infused by its weight. In addition, the infusion rate of the medical liquid is controlled in such a manner that a user adjusts the medical liquid regulator so that the drop period of the droplets 23 can be changed, and the user checks the drop period by counting the number of droplets while seeing the droplets by the naked eye and measuring the length of consumed time with an ordinary watch. In general, a doctor writes the number of droplets dropping per minute on a chart, or writes the quantity of medical liquid to be infused per hour or per day on the chart in CC unit, so that a nurse regulates the drop rate of the droplets in accordance with the above-mentioned method.

However, since the above-mentioned medical liquid infusion rate regulating method is conducted on the basis of the user's eyes and experience, it is impossible to correctly regulate the medical liquid infusion rate. In general, although the medical liquid should be infused in a precisely regulated rate depending on the age and condition of a patient, the type of medical liquid, and the medicaments contained in the medical liquid, the above-mentioned medical liquid infusion method may incorrectly regulate the medical liquid infusion rate, which may cause a medical malpractice.

Accordingly, it is necessary to quantitatively measure the medical liquid infusion rate so as to adjust the medical liquid regulator 30. For this purpose, the prior art has proposed in Korean Un-examined Patent Publication No. 10-2004-0048889, entitled "Volumetric Flow Measuring Apparatus for intravenous Injection Set," and Korean Un-examined Patent Publication No. 10-2005-0039780, entitled "System for Measuring Flow Rate of Ringer's solution Using Image Signal Processing." However, since the apparatus and system measure the number of dropping droplets 23 and the quantity of medical liquid by sensing the droplets 23 dropping in the drip chamber with infrared (IR) rays, they not only lack accuracy due to the influence of external light, but also cause inconvenience and costs in connection with installing the measuring apparatus or system, by which the apparatus or system have not been actually produced on a market scale.

In addition, Korean Registered Utility Model Publication 20-0336940, entitled "Automatic Detection and Prevention System of Drug Dripper," proposed an apparatus provided with a drop carrier which is moved each time when a droplet drops in a drip chamber, so that the dropping of droplets can be sensed from the outside. However, the apparatus has not been practically used since it is necessary to change the typically used drip chamber 22 in terms of construction, and its drip chamber and measuring device are very complicated.

In addition, since the above-mentioned conventional technologies basically use a volume measuring method by means of a sensor, the infusion rate of medical liquid cannot help being regulated, only depending on the measuring device. Therefore, since it is difficult to cope with the malfunction of such a measuring device, what is needed is a simple and convenient measuring device which does not suffer from minor troubles when it is used by a doctor in charge or a nursing staff.

As the above-mentioned prior art systems, apparatuses and devices have not been practically used due to their own problems, a nursing staff in a clinic or hospital calculates medical liquid infusion rate by measuring the length of drop time of droplets with a stopwatch by a predetermined number of times. In such a method, since it is necessary to check the stopwatch and the drip chamber 22 while alternately watching them, a large error may occur in terms of calculated infusion rate. Therefore, what is needed is a medical liquid infusion rate measuring device which can be easily used by a non-skilled nursing staff.

For this purpose, in Korean Patent No. 10-0706945, entitled "medical liquid Infusion Rate Measuring Device," the present applicant proposed an apparatus capable of measuring medical liquid infusion rate by receiving inputs of droplet drop period by a set number of times.

In addition, in Korean Patent No. 10-0872089, entitled "medical liquid Infusion Supporting Device," the present applicant proposed a medical liquid infusion supporting device which calculates the quantity of medical liquid infused per unit time on the basis of the preset volume of a droplet, thereby determining the drop period of droplets, and outputting acoustic waves in accordance with the determined drop period, so that the drip interval can be regulated.

However, prescriptions for medical liquid infusion are frequently rendered in relation to the quantity of medical liquid to be infused and the length of time for infusion, although such prescriptions are occasionally rendered in relation to the quantity of medical liquid to be infused per unit time (cc/hr or gtt/min). Therefore, the above-mentioned systems, apparatuses and devices have problems in that there are difficulties in that a nursing staff should calculate the quantity of medical liquid to be infused and the length of time for infusion through mental arithmetic or the like, convert them into information for the quantity of medical liquid to be infused per unit time, and then input the information, and furthermore, if there is an error in calculation, a medical malpractice may be caused. Therefore, what is needed is a device which can output a drip period, even if the information for the quantity of medical liquid and the length of time for infusion, rather than the information for the infusion quantity of medical liquid per unit time, is input.

Meanwhile, the above-mentioned systems, apparatuses and devices have employed a method of measuring medical liquid infusion rate, which is executed in such a manner that if a user pushes a count input key to be inconsistent with a drip period by mistake, the user recognizes the error, re-pushes the count input key by a preset number of times, and then measures the medical liquid infusion rate. However, since the method relies only on the user's judgment in checking the drip interval, there is a problem in that if the user completes the measurement of medical liquid infusion rate without recognizing an error caused at the time of determining the count input time interval, the error cannot help increasing the error range, even if the error is trivial, due to the characteristic of the systems, apparatuses and devices that determine the number of droplets, which is proportional to the length of consumed time as the length of time consumed for conducting count inputs in relation to the number of count input times.

SUMMARY OF THE INVENTION

Accordingly, the present invention has been made to solve the above-mentioned problems occurring in the prior art, and an object of the present invention is to provide a portable medical liquid infusion device which can provide more correct measuring results by limiting the erroneous measuring results caused by an erroneous input when measuring the infusion rate of medical liquid.

Another object of the present invention is to provide a portable medical liquid infusion device which can calculate and show a length of time for infusion corresponding to the remaining quantity of medical liquid when measuring the infusion rate of the medical liquid.

Another object of the present invention is to provide a portable medical liquid infusion device which allows a user to know a drip interval not only by inputting medical liquid infusion rate but also by inputting the quantity of the medical liquid and the length of infusion time, whereby input methods can be diversified and hence the medical liquid regulator can be easily regulated in accordance with the drip interval.

In order to accomplish this object, there is provided a portable medical liquid infusion device for quantitatively measuring medical liquid infusion rate, and notifying the medical liquid infusion rate by a droplet drop period, the infusion device including: a key input unit which receives a selection of an infusion rate control mode or an infusion rate measuring mode, receives an input of the quantity of medical liquid infused per unit time, receives a count input from a user each time when a droplet drops downward in a drip chamber, and receives a selection of a droplet volume according to the use of the medical liquid; a display unit which outputs the quantity of the medical liquid and a length of infusion time input by the user at the infusion rate control mode so that the user can confirm the quantity of the medical liquid and the length of infusion time, and quantitatively outputs the supply rate of the medical liquid calculated at the infusion rate measuring mode; a speaker which outputs acoustic waves of a predetermined period at the infusion rate control mode; an oscillating unit for oscillating electric signals of a predetermined frequency; a power supply unit for supplying power; and a control unit, wherein at the infusion rate control mode, the control unit determines the drop period of droplets by dividing the quantity of the medical liquid infused per unit time, which is input through the key input unit, by the droplet volume selected through the key input unit, and outputs acoustic waves corresponding to the drop period of droplets to the speaker using the electric signal frequency of the oscillating unit, and at the infusion rate measuring mode, the control unit calculates the length of time consumed for receiving count inputs by the preset number of times after the droplet volume is selected, on the basis of the electric signal frequency of the oscillating unit, converts the preset number of times into the number of droplets per unit time by substituting the calculated length of time, determines the quantitative medical liquid infusion rate by multiplying the preset droplet volume and the converted number of droplets per unit time, and outputs the determined infusion rate to the display unit, and wherein at the infusion rate measuring mode, the control unit calculates a mean value for the count input time intervals of the previous step, and calculates the ratio of the current count input time interval in relation to the calculated mean value, and if the calculated ratio is out of a preset range, the control unit determines the infusion rate by calculating the length of time consumed for count inputs of the preset number of times to be received thereafter.

In accordance with the present invention, the inventive portable medical liquid infusion device can be used not only by inputting a medical liquid infusion rate, but also by inputting information for the quantity of medical liquid to be infused, the length of time for infusion, and a droplet volume, and the drip interval can be regulated while directly watching the drip chamber and with reference to the acoustic signals outputted in accordance with the calculated drip rate. Therefore, an unskilled nursing staff can easily regulate the medical liquid regulator without any calculation error.

In addition, when a count input is conducted so as to measure the infusion rate of currently infused medical liquid, the present invention compares the count input time interval of the previous step with the count input time interval of the current step, and judges a count input irregularly input beyond a preset reference time interval as an erroneous input and conducts initialization. Therefore, the present invention can prevent the occurrence of an erroneous measuring result caused by an erroneous input at the time of measuring infusion rate, thereby enhancing the reliability for the count input, and measuring the medical liquid infusion rate more precisely.

In addition, the present invention outputs the length of remaining infusion time corresponding to the quantity of medical liquid from the determined quantity of medical liquid per unit time if the quantity of medical liquid is input when the medical liquid infusion rate measuring mode is initiated or the measurement is completed. Therefore, it is possible to know when the IV injection system should be separated from a patient or when the medical liquid bottle should be replaced, without needing to calculate the length of remaining infusion time.

BRIEF DESCRIPTION OF THE DRAWINGS

The above and other objects, features and advantages of the present invention will be more apparent from the following detailed description taken in conjunction with the accompanying drawings, in which:

FIG. 1 shows a construction of a conventional intravenous injection system;

FIG. 2 is a block diagram of a portable medical liquid infusion device 100 in accordance with an embodiment of the present invention; and FIG. 3 is a flowchart for the steps conducted by the medical liquid infusion device of FIG. 2.

DETAILED DESCRIPTION OF THE PREFERRED EMBODIMENTS

Hereinafter, a preferred embodiment of the present invention will be described with reference to the accompanying drawings. In the following description and drawings, the same reference numerals are used to designate the same or similar components, and so repetition of the description on the same or similar components will be omitted.

Portable Medical Liquid Infusion Device

FIG. 2 is a block diagram of a portable medical liquid infusion device 100 in accordance with an embodiment of the present invention.

The portable medical liquid infusion device 100 shown in FIG. 2 includes a key input unit 120, a display unit 130, a speaker 140, an oscillating unit 150, a power supply unit 160, and a control unit 110.

The key input unit 120 includes: a mode selection key 121 for selecting a medical liquid infusion rate control mode or a medical liquid infusion rate measuring mode; an infusion rate input key 122 for inputting the quantity of medical liquid to be infused per unit time at the medical liquid infusion rate control mode; a medical liquid quantity input key 123 for inputting the quantity of medical liquid to be infused; an infusion time input key 124 for inputting the length of time for infusing medical liquid; a count input key 126 for allowing a user to input a count each time when a droplet 23 drops within a drip chamber 22 at the infusion rate measuring mode; and a droplet selection key 125 for selecting a droplet volume according to the use of the medical liquid. Meanwhile, in the key input unit 120, the infusion rate input key 122, the medical liquid quantity input key 123, and the infusion time input key 124 may be configured in various forms. For example, in the key input unit 120, the infusion rate input key 122, the medical liquid quantity input key 123 and the infusion time input key 124 may be implemented as a selection key (not shown) or an up-down key, so that any item can be selected among various items (the quantity of medical liquid to be infused per unit time, the quantity of medical liquid, and the length of infusion time) through the selection key, and then the quantity is regulated and input by manipulating the up-down key. Alternatively, the selection key and the up-down key may be implemented in such a manner that each time when the selection button is pushed after the infusion rate control mode is selected, the input state is sequentially changed to the medical liquid quantity input state, and the infusion time input state from the infusion rate input state, or if the selection button is pushed after the infusion rate measuring mode is selected, the quantity of medical liquid can be input. Like this, the inventive key input unit 120 is not limited to the above-mentioned construction.

The display unit 130 displays the quantity of medical liquid and the length of infusion time input by the user at the infusion rate control mode, so that the user can confirm them again, and the display unit 130 quantitatively outputs the supply rate of medical liquid calculated at the infusion rate measuring mode.

The speaker 140 outputs acoustic waves with a predetermined period corresponding to the drip interval at the infusion rate control mode.

The oscillating unit 150 oscillates electric signals with a predetermined frequency.

The power supply unit 160 supplies power to each of the above-mentioned components.

If the infusion rate control mode or the infusion rate measuring mode is selected through the key input unit 120, and information required for implementing the selected operation mode is input to the control unit 110, the control unit 110 processes the input information and controls the above-mentioned components 130, 140 and 150 so that the components implement the corresponding operation mode.

Now, the operations of the control unit 110 conducted in each operation mode will be described in more detail.

Infusion Rate Control Mode

The infusion rate control mode is an operation mode in which the control unit 110 receives an input of information for medical liquid infusion rate per unit time (cc/hr) or information for the quantity of medical liquid to be infused and the length of time for infusing the medical liquid, and an input of information for a droplet volume, and calculates a corresponding drop period of droplets 23, which is outputted with sounds. The reason why the information for the quantity of medical liquid and the length of time for infusing the medical liquid is input beyond the information for the quantity of medical liquid to be infused per unit time is because when orders for the infusion of medical liquid are rendered, the orders are frequently rendered for the quantity of medical liquid to be infused and the length of time for infusing the medical liquid, although the orders may be rendered for the quantity of medical liquid to be infused per unit time (cc/hr). Therefore, in accordance with an embodiment of the present invention, the key input unit 120 is provided with an infusion rate input key 122 so as to receive an input of information for the quantity of medical liquid to be infused per unit time (cc/hr) as information for calculating a drip period, and the key input unit 120 is additionally provided with a medical liquid quantity input key 123 and an infusion time input key 124 so as to use the information for the quantity of medical liquid to be infused and the length of time for infusing the medical liquid as information for calculating the drip period.

If the infusion rate control mode is selected through the mode selection key 121, a droplet volume is selected through the droplet selection key 125, and the quantity of medical liquid to be infused per unit time is input through the infusion rate input key 122, the control unit 110 calculates the drop period of the droplets 23 by dividing the quantity of medical liquid to be infused per unit time by the droplet volume, and then receives signals with a predetermined frequency from the oscillating unit 150, thereby generating acoustic wave signals with the calculated period, wherein the acoustic wave signals are outputted through the speaker 140.

In addition, if the control unit is in a state in which the quantity of medical liquid is input through the medical liquid quantity input key 123 when the quantity of medical liquid to be infused per unit time is input, the control unit 110 divides the quantity of medical liquid by the quantity of medical liquid to be infused per unit time, thereby determining the length of time for infusing the medical liquid, which is outputted to the display unit 130.

Meanwhile, if the control unit 110 receives an input the quantity of medical liquid to be infused and the length of time for infusing the medical liquid through the medical liquid quantity input key 123 and the infusion time input key 124, respectively, rather than the quantity of medical liquid to be infused per unit time, which is input through the infusion rate input key 122, the control unit 110 divides the quantity of medical liquid by the length of time for infusing the medical liquid, thereby determining the quantity of medical liquid to be infused per unit time, and then calculates the drop period of the droplets 23.

At this time, the user can easily and conveniently regulate the drop period of the droplets in accordance with the acoustic wave signals outputted with the calculated period, using the medical liquid regulator 30. The inventive portable medical liquid infusion device 100 operated in the infusion rate adjusting mode in this manner allows the user to easily and conveniently adjust the real drip period of droplets 23 in the drip chamber 20 in accordance with the calculated drop period by manually adjusting the medical liquid regulator 30 while aurally listening the drip period signals as well as visually seeing the dropping droplets 23.

In addition, the portable medical liquid infusion device 100 may further include a vibrating device (not shown) or a light emitting device (not shown) as means for notifying period signals so that the drip period of droplets can be easily sensed even in a very noisy place or the like.

Infusion Rate Measuring Mode

The infusion rate measuring mode is a mode in which the control unit 110 outputs the medical liquid infusion rate and the length of time for infusing the remaining medical liquid by calculating the drip period of the droplets 23 in accordance with counter signals input by the user each time when a droplet 23 drops within the drip chamber 22.

If the infusion rate measuring mode is selected through the mode selection key 121 and the droplet volume is selected through the drip selection key 125, the control unit 110 executes the infusion rate measuring mode. That is, if counter signals, each of which is input by the user each time when a droplet drop in the drip chamber 22 is input through the count input key 126, the control unit 110 calculates the length of time consumed until the count inputs are conducted by a preset number of times, and converts the preset number of times into the number of droplets per one hour. Then, the control unit 110 multiplies the input droplet volume and the converted number of droplets, and thus determines the quantity of medical liquid to be infused per unit time, wherein the control unit 110 outputs the quantity of medical liquid to be infused per unit time through the display unit 130.

In addition, if the count inputs are conducted in excess of the preset number of times, the control unit 110 determines the medical liquid infusion rate on the basis of the most recent count input corresponding to the preset number of times. That is, the count inputs used for calculating the medical liquid infusion rate include the current count input and the count inputs which were most recently received prior to the current count input, and the number of which is smaller than the preset number of times by one (1). In addition, the control unit 110 calculates and converts the length of time consumed for such count inputs into the number of droplets per one hour, and determines the quantity of medical liquid to be infused per unit time.

Meanwhile, if the control unit 110 is in a state in which the quantity of medical liquid to be infused is input through the medical liquid quantity input key 123 when the infusion rate measuring mode and the drop volume are selected, the control unit 110 determines the quantity of medical liquid to be infused per unit time, and then also determines the length of time for infusing the remaining medical liquid by dividing the quantity of medical liquid by the quantity of medical liquid to be infused per unit time, wherein the control unit 110 outputs the length of time to the display unit 130 together with the quantity of medical liquid to be infused per unit time.

In addition, even if the quantity of medical liquid is input after the quantity of medical liquid to be infused per unit time determined as described above is outputted to the display unit 130, the control unit 110 may be configured in such a manner that it determines the length of time for infusing the remaining medical liquid by dividing the input value of the quantity of medical liquid by the determined value of the quantity of medical liquid to be infused per unit time, and outputs the length of time for infusing the remaining medical liquid to the display unit 130. That is, by storing the determined value of the quantity of medical liquid to be infused per unit time in a memory (not shown), the control unit 110 is adapted to calculate and output the length of time for infusing the remaining medical liquid if the value of the quantity of medical liquid is input.

In addition, the control unit 100 may be preferably configured in such a manner that it also stores the calculated length of time for infusing the remaining medical liquid, and outputs an alert sound through the speaker 140 at a time point corresponding to the lapse of the length of time for infusing the remaining medical liquid, or at a time point prior to the lapse of the length of time for infusing the remaining medical liquid by a preset length of time, so that the time point for completing the infusion of medical liquid can be notified. For this purpose, the control unit 110 may check the lapse of the length of time for infusing the medical liquid using the predetermined frequency of the oscillating unit 150, and may output the alert sound through the speaker 140 if it arrives at the time point corresponding to the lapse of the length of time for infusing the remaining medical liquid or at a time point determined by subtracting a preset length of time from the length of time for infusing the remaining medical liquid. In addition, in order to manage two or more patients with a single device, the control unit 110 is preferably configured in such a manner that if a hospital room number or a patient identification number is input after calculating the length of time for infusing the remaining medical liquid for a patient, the control unit 110 stores the input number to correspond to the length of time for infusing the remaining medical liquid for the patient, and also outputs the corresponding number to the display unit 130 when outputting the alert sound at a time corresponding to the lapse of the length of time for infusing the remaining medical liquid.

In addition, when the count inputs are conducted through the count input key 126, the control unit 110 calculates the mean value of the count input time intervals in the previous step, calculates the ratio of the current count input time interval in terms of the calculated mean value, and then compares the calculated ratio with a preset range. If the calculated ratio is out of the preset range, the control unit 110 initializes the count input, and renders another count input to be conducted again, and at the same time, the control unit 110 notifies the user with a beep or vibration that the initialization has been conducted. Here, the preset range may be properly set through repeated tests, and may be set, for example, as 0.7 to 1.3. If it is determined that the calculated ratio is out of the preset range, it means that the user erroneously operates the count input key much faster or much more slowly as compared to the drip interval. Therefore, the count input is considered as an erroneous input and thus initialized.

As described above, the present invention determines whether a count input is an erroneous input or not by comparing the count input time interval at the previous step with the current count input time interval. It should be noted that although the present embodiment uses the mean value of the count input time intervals made till the previous step as the reference for determination, the present is not limited to this.

For example, the control unit 110 may be configured in such a manner that if the ratio of the current count input time interval in relation to the count input time interval at the just previous step is out of the preset range, the control unit 110 determines the current count input as an erroneous input, and initializes the count input.

In addition, the control unit 110 may be configured in such a manner that the control unit 110 is capable of presetting an error range, of detecting the maximum count input time interval and the minimum count input time interval among the count input time intervals till the previous step, and the current count input time interval, and of confirming whether an error determined by subtracting the minimum count input time interval from the maximum count input time interval is included in the preset error range, thereby determining whether a count input is an erroneous input or not. At this time, the error range may be preferably determined by multiplying a preset ratio by the count input time interval of the previous step at each input time.

In addition, the control unit 110 may be configured in such a manner that the control unit is capable of setting the upper and lower limits with reference to the initial count input time interval, and of confirming whether the count input time interval determined after determining the initial time interval is positioned within the upper and lower limits, thereby determining whether the count input is an erroneous input.

Now, a description for the droplet volumes selected through the droplet selection key 125 will be additionally made. In general, the dripper 20, the medical liquid regulator 30, the infusion tube 40, and the injection needle 50 are fabricated in a single body as an infusion set, wherein the sizes of the insertion needle 21 and the drip chamber 22 are determined in such a manner that the droplets 23 dropping downward within the drip chamber 22 through the insertion needle 21 have a constant volume. For example, an infusion set for administrating an ordinary medical liquid is fabricated to drip 20 droplets per 1 ml, and a volume control infusion set (micro drip set) is fabricated to drip 60 droplets per 1 ml. In addition, an infusion set for administrating a special medical liquid, such as a nutrition medical liquid, is fabricated to drip droplets having the same volume with those of the ordinary medical liquid when it is provided as one set with an infusion container. The infusion set is fabricated in this manner so as to allow the user to know the infusion rate by measuring infusion time using an ordinary clock while visually checking dropping droplets.

Therefore, the volumes of droplets designated and stored in the control unit 110 may be set as the droplet volumes that are usually used, like ½₀ ml or ¹⁄₆₀ ml. Preferably, by showing an information indication, such "Ordinary(20)", or "Control infusion Set (60)," using an indication lamp, it is possible to prevent a medical malpractice.

In addition, since an infusion set may be configured to drip 10, 20 or 30 droplets per 1 ml rather than 20 or 60 droplets per 1 ml, the droplet volumes to be selected through the droplet selection key 125 may consist of ½₀ ml, ¹⁄₆₀ ml, ¹⁄₁₀ ml, ¹⁄₁₅ ml and ¹⁄₃₀ ml, wherein it is desired if a droplet volume selected through the droplet selection key 125 is set in accordance with the characteristics of the infusion set.

In addition, the display unit 130 may further include a box-line so that it can emphasize and indicate anyone of the above-mentioned values to be set.

Infusion Rate Measuring Method

FIG. 3 shows an infusion rate measuring method using a device having the configuration shown in FIG. 2.

It should be noted that in the following description for the infusion rate measuring method described, it is assumed that the preset number of times is 4 times, and the length of time measured between the first count input and the fifth count input indicates the length of time required for dripping 4 droplets in total.

At first, the user turns on the power key of the key input unit 120, so that power can be supplied to individual components of the portable medical liquid infusion device 100 from the power supply unit 140. At this time, the portable medical liquid infusion device 100 is initialized so as to calculate medical liquid infusion rate. In addition, if the user pushes a reset key, the portable medical liquid infusion device 100 is also initialized for the medical liquid infusion rate measuring process described below (P1).

The portable medical liquid infusion device 100 initialized in this manner initiates the checking of count input intervals through the count input key if the user inputs the count input key as the first droplet 23 drops, and initializes the number of times of inputting the count input key (the number of counts) as 0 (P10).

In addition, the portable medical liquid infusion device 100 compares the number of count inputs with the preset number of times (4 times) (P21), and each time when a droplet drops downward within the drip chamber 22, the portable medical liquid infusion device 100 receives one (1) input of the count input key (P22). The portable medical liquid infusion device 100 calculates the mean count input time interval till the previous step, calculates the ratio of the current count input time interval in relation to the mean count input time interval, and confirms whether the calculated ratio is included in the preset range. If it is confirmed that the calculated ratio is included in the preset range, the portable medical liquid infusion device 100 returns to the step for receiving count input (P21), and if it is confirmed that the calculated ratio is out of the preset range, the portable medical liquid infusion device 100 determines that the count input is an erroneous input, and conducts the initialization of P10 (P23). However, it should be noted that since the count input time intervals are generated from the second count input, and the count input time intervals till the previous step are generated from the third count input, in the erroneous input determining step (P23) is conducted from the third count input.

If the number of times of inputting the count input key (the number of counts) arrives at the preset number of times (4 times) by repeatedly conducting the above-mentioned steps P21, P22 and P23, the infusion rate calculating step (P20) is conducted.

Next, the portable medical liquid infusion device 100 calculates the length of time consumed for inputting the count input key four times (P30), converts the number of droplets for the consumed length of time determined through calculation into the number of droplets per one hour (P40), calculates quantitative infusion rate (ml/hr) on the basis of the designated droplet volume and the converted number of droplets per one hour, calculates the length of time for infusing the remaining medical liquid by dividing the quantity of medical liquid to be infused by the calculated infusion rate (ml/hr), and outputs the infusion rate and the remaining infusion time through the display unit 130 (P50).

In addition, after the step P50, the portable medical liquid infusion device 100 confirms whether there is an input of the count input key for additionally checking the infusion rate (P61), and if it is confirmed that there is an input of the count input key, the portable medical liquid infusion device 100 stores the count input time interval, and simultaneously deletes the information for the first count input, so that the infusion rate can be re-calculated only on the basis of the count input information of the preset number of times (4 times) (P62).

Next, the portable medical liquid infusion device 100 calculates the ratio of the current count input time interval in relation to the mean count input time interval till the previous step, and determines whether the calculated ratio is included in the preset range. If it is determined that the calculated ratio is included in the preset range, the portable medical liquid infusion device 100 returns to the step P30 for calculating the length of time consumed for the count inputs, and if it is determined that the calculated ratio is out of the preset range, the portable medical liquid infusion device 100 determines the count input as an erroneous input and conducts the initialization of the step P10 (P63).

Since the length of time from the time point when the first droplet drops to the time point when the fifth droplet drops in the step P10 in the process of counting the number of dropping droplets 23 is checked in the step of calculating the length of time consumed for count input (P30), the length of time consumed while the first droplet is dropping is excluded from the calculation. Therefore, it is possible to remove the problem that the length of time from the time point when the droplet just prior to the first droplet drops to the time point when the first droplet drops may be varied depending on users. In addition, if a user continuously conducts a count input through the count input key each time when a droplet 23 drops as in the step P60 where the user adds a count input, considering that infusion rate is incorrectly determined through the count inputs of five times in total, the portable medical liquid infusion device 100 re-calculates and outputs the infusion rate for four (4) droplets each time when a count input is conducted. For example, assuming the count input key is input for seven droplets in total, when the fifth input is conducted, the infusion rate for the second, third, fourth and fifth droplets 23 are calculated and outputted to the display unit 130, when the sixth input is conducted, the infusion rates for the third, fourth, fifth and sixth droplets 23 are calculated and outputted to the display unit 130, and when the seventh input is conducted, the infusion rates for the fourth, fifth, sixth and seventh droplets 23 are calculated and outputted to the display unit 130.

Meanwhile, if the count inputs are irregularly conducted in such a manner that one or more count input time intervals are positioned out of an error range, the initialization (P10) is conducted so that count inputs shall be conducted again from the beginning. As a result, it is possible to minimize the occurrence of erroneous measuring results caused by erroneous inputs at the time of measuring the infusion rate. Consequently, it is possible to enhance the reliability for count inputs, and to measure the infusion rate more precisely.

Although the above description was made assuming that droplets 23 drip four times in total, the number of times of dripping droplets can be designated in order to enhance the accuracy of the measuring device 100, and in consideration of the length of time consumed for a measuring process.

In addition, although it was described that the embodiment of FIG. 3 stores the drop time intervals of droplets 23 so as to calculate the length of time consumed for the preset number of times (4 times), it is possible to calculate the length of time by storing the length of time at a time point when a droplet drops. That is, it is possible to calculate the length of time consumed for dripping droplets four times by subtracting the length o time at the first input time point from the length of time at the fifth input time point.

In addition, if an input of the reset key is received, the portable medical liquid infusion device 100 starts again from the step P10.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A portable medical liquid infusion device for quantitatively measuring medical liquid infusion rate, and notifying the medical liquid infusion rate by a droplet drop period, the infusion device comprising: a key input unit (120) which receives a selection of an infusion rate control mode or an infusion rate measuring mode, receives an input of the quantity of medical liquid infused per unit time, receives a count input from a user each time when a droplet (23) drops downward in a drip chamber (22), and receives a selection of a droplet volume according to the use of the medical liquid; a display unit (130) which outputs the quantity of the medical liquid and a length of infusion time input by the user at the infusion rate control mode so that the user can confirm the quantity of the medical liquid and the length of infusion time, and quantitatively outputs the supply rate of the medical liquid calculated at the infusion rate measuring mode; a speaker (140) which outputs acoustic waves of a predetermined period at the infusion rate control mode; an oscillating unit (150) for oscillating electric signals of a predetermined frequency; a power supply unit (160) for supplying power; and a control unit (110), wherein at the infusion rate control mode, the control unit (110) determines the drop period of droplets by dividing the quantity of the medical liquid infused per unit time, which is input through the key input unit (120), by the droplet volume selected through the key input unit (120), and outputs acoustic waves corresponding to the drop period of droplets to the speaker (140) using the electric signal frequency of the oscillating unit (150), and at the infusion rate measuring mode, the control unit (110) calculates the length of time consumed for receiving count inputs by the preset number of times after the droplet volume is selected, on the basis of the electric signal frequency of the oscillating unit (150), converts the preset number of times into the number of droplets per unit time by substituting the calculated length of time, determines the quantitative medical liquid infusion rate by multiplying the preset droplet volume and the converted number of droplets per unit time, and outputs the determined infusion rate to the display unit (130), and wherein at the infusion rate measuring mode, the control unit (110) calculates a mean value for the count input time intervals of the previous step, and calculates the ratio of the current count input time interval in relation to the calculated mean value, and if the calculated ratio is out of a preset range, the control unit determines the infusion rate by calculating the length of time consumed for count inputs of the preset number of times to be received thereafter.

2. The portable medical liquid infusion device as claimed in claim 1, wherein the key input unit (120) is configured to be capable of receiving an input of the infusion quantity to be infused, and the length of time for infusion, and wherein if an input of the infusion quantity and the length of time for infusion is received instead of an input of infusion quantity per unit time at the infusion rate measuring mode, the control unit (110) determines the infusion quantity per unit time by dividing the infusion quantity by the length of time for infusion, and conducts an operation for outputting acoustic wave corresponding to the infusion quantity per unit time, and wherein if an input of a value of the infusion quantity is received at the infusion rate measuring mode, the control unit (110) determines the length of time for infusion by dividing the input value of the infusion quantity by the infusion rate and outputs the length of time for infusion to the display unit (130), and then the control unit (110) outputs an alert sound through the speaker (140) at a time point corresponding to the lapse of the length of time for infusion, or at a time point determined by subtracting a preset length of time from the length of time for infusion, and if one or more count inputs in excess of the predetermined number of times are received, the control unit calculates the consumed length of time on the basis of count inputs most recently received and corresponding to the preset number of times, including the finally received count input, thereby determining the infusion rate.

3. A method for calculating infusion rate using a portable medical liquid infusion device which receives a count input from a user each time when a droplet (23) drops downward in a drip chamber (22), calculates a consumed length of time if the count input is received by a predetermined number of times, and determines quantitative medical liquid drip rate according to a previously designated droplet volume, wherein the method comprises the steps of: initiating the checking of a count input time interval when the first count input is received (P10); continuously receiving count inputs by a preset number of times after the first count input, and storing a count input time interval is stored each time when a count input is received (P20); calculating the length of time for receiving the count inputs by the preset number of times (P30); converting the preset number of times for the calculated length of consumed time into the number of droplets per one hour (P40); calculating the infusion quantity per one hour by multiplying the designated droplet volume and the number of droplets per one hour, and outputting the infusion quantity per one hour (P50); and storing a new count input time interval if a count input is received within a designated length of time after the step P50, and returning to the step P30 to delete the first count input time interval among the count inputs used in the calculation in the step P30, and to include the new count input time interval (P60), wherein each of the count input receiving step (P20) and the new count input time interval storing step (P60) further comprises: the step of calculating the mean value of the count input time intervals stored till the step just prior to the current count input, and returning to the checking initiating step (P20) if the ratio of the current count input time interval in relation to the mean value of the count input time intervals is out of a preset range (P23, 63).

* * * * *